(12) United States Patent
Tokuda et al.

(10) Patent No.: US 6,696,609 B2
(45) Date of Patent: Feb. 24, 2004

(54) PROCESS FOR PRODUCING DIAMINES

(75) Inventors: Yoshihiro Tokuda, Kurashiki (JP); Shigeaki Suzuki, Osaka (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 10/377,828

(22) Filed: Mar. 4, 2003

(65) Prior Publication Data

US 2003/0187303 A1 Oct. 2, 2003

(30) Foreign Application Priority Data

Mar. 27, 2002 (JP) ........................................ 2002-087552

(51) Int. Cl.[7] ............................................... C07C 29/26
(52) U.S. Cl. ........................ 564/397; 564/398; 564/473
(58) Field of Search ................................ 564/397, 398, 564/473

(56) References Cited

U.S. PATENT DOCUMENTS 5,973,208 A  10/1999  Nagareda et al.

OTHER PUBLICATIONS

Data CAPLUS on STN, Acc. No. 1993:448935, Iguchi, JP 05017413, Jan. 26, 1993, abstract.*
Database CAPLUS on STN, Acc. No. 1995:412857, Kos, DE 4322065, Jan. 12, 1995, abstract.*

* cited by examiner

*Primary Examiner*—Brian Davis
(74) *Attorney, Agent, or Firm*—Oblon, Spivak, McClelland, Maier & Neustadt, P.C.

(57) ABSTRACT

A process for producing diamines which comprises the steps of: (1) reacting a dialdehyde with ammonia and hydrogen in the presence of an alcohol and a hydrogenation catalyst to synthesize the corresponding diamine; (2) separating and recovering the alcohol by distilling the reaction mixture obtained by the step (1); (3) separating the diamine by purifying the distillation residue obtained by the step (2); and (4) feeding at least part of the alcohol recovered in the step (2) to step (1); said step (1) comprising maintaining the amount of ammonia at a level of at least 200 moles per mole of the primary amine that has formed in the step (1) and accumulated in the reaction vessel for step (1). The process can produce diamines commercially advantageously and in high yields, the diamines having little impurities.

19 Claims, No Drawings

PROCESS FOR PRODUCING DIAMINES

BACKGROUND OF THE INVENTION

1. Field of the Invention

The present invention relates to a process for producing diamines from the corresponding dialdehydes. The diamines produced by the process of the present invention are useful as starting materials for polyamides, polyurethanes and like polymers, as well as starting materials for various chemicals.

2. Description of the Related Art

Various processes are known for producing diamines by reacting a dialdehyde with ammonia and hydrogen in the presence of a hydrogenation catalyst, as exemplified below.

(1) U.S. Pat. No. 2,636,051 discloses a process which comprises feeding a dialdehyde to a reaction vessel containing ammonia, hydrogen and a hydrogenation catalyst, at a rate which does not exceed the consumption rate of the dialdehyde, and shows an example where a diamine was obtained in a yield of 60%, with use of a catalyst of Raney nickel and a solvent of water.

(2) Japanese Patent Application Laid-open No. 17413/1993 discloses a process which comprises feeding an alcoholic solution of a dialdehyde to a reaction zone containing a hydrogenation catalyst, a solvent, hydrogen and ammonia, and shows, in its examples that a diamine was obtained in a yield of 86.9 to 91.6%, with use of a catalyst of Raney nickel and a solvent of methanol or ethanol, and that no use of such an alcohol caused the reaction liquid to polymerize, thus yielding no desired product at all.

(3) Japanese Patent Application Laid-open No. 69999/1995 (U.S. Pat. No. 5,475,141 and EP 0 628 535 A1) discloses a process which comprises preparing a mixture of a dialdehyde and a diluting agent such as an alcohol while adjusting the mixing temperature at 5° C. or below, thereby suppressing formation of hemiacetal, and then feeding the mixture to a reductive amination vessel. In the examples, 1,8-octanediamine was obtained from a dialdehyde of 1,8-octanedialdehyde with a catalyst of nickel supported on silica/alumina and a diluting agent of methanol, toluene or methyl t-buthyl ether, in a yield of 95%, 90.1% or 87.8%, respectively.

(4) Japanese Patent Application Laid-open No. 196586/1995 discloses a process which comprises using as a hydrogenation catalyst a nickel supported on an inorganic oxide. In the examples, a mixture of 1,9-nonanedial and 2-methyl-1,8-octanedial as dialdehydes yielded, with use of a catalyst of nickel supported on Kieselguhr and a solvent of 1-butanol, methanol, 2-propanol, tetrahydrofuran or 1,4-dioxane, a mixture of 1,9-nonanediamine and 2-methyl-1,8-octanediamine in a yield of 92.6%, 93.5%, 89.0%, 92.1% or 91.2%, respectively.

(5) Japanese Patent Application Laid-open No. 130210/1998 discloses a process which comprises dissolving a dialdehyde in a lower alcohol in the presence of an amine other than ammonia in an amount of not more than 4 mole % based on the moles of the dialdehyde and then subjecting the solution to reductive amination. In the examples, mixtures of 1,9-nonanedial and 2-methyl-1,8-octanedial as dialdehydes yielded, with use of a catalyst of Raney nickel and a solvent of methanol, by addition of an amine such as triethylamine, mixtures of 1,9-nonanediamine and 2-methyl-1,8-octanediamine in a maximum yield of 95%.

(6) Japanese Patent Application Laid-open No. 310559/1998 discloses a process which comprises carrying out reductive amination with use of a solvent of an alcohol having 3 to 10 carbon atoms. In the examples, a mixture of 1,9-nonanedial and 2-methyl-1,8-octanedial as dialdehydes using a catalyst of Raney nickel yielded, with use of a solvent of n-butanol, isopropyl alcohol or n-octyl alcohol, a mixture of 1,9-nonanediamine and 2-methyl-1,8-octanediamine at a yield of 90.5%, 92.0% or 90.8%, respectively. In another example, there were used the same starting material, a catalyst of nickel supported on Kieselguhr and a solvent of n-butanol, to yield a mixture of 1,9-nonanediamine and 2-methyl-1,8-octanediamine at a yield of 97%. Still another example started from a dialdehyde of 3(4),8(9)-tricyclo[5.2.1.0]decanedicarbaldehyde with use of Raney nickel catalyst and a solvent of n-butanol, and obtained tricyclodecanedimethanamine in a yield of 91.6%.

(7) Japanese Patent Application Laid-open No. 29534/1999 (U.S. Pat. No. 5,973,208 and EP 0 878 462 B1) discloses a process which comprises carrying out the reaction, with use of a solvent of an alcohol, while adjusting the water concentration in the liquid phase in the reaction vessel within the range of 5 to 15% by weight. In the examples, a mixture of 1,9-nonanedial and 2-methyl-1,8-octanedial as dialdehydes using a catalyst of Raney nickel yielded, with use of a solvent of n-butanol, methanol or isoamyl alcohol, a mixture of 1,9-nonanediamine and 2-methyl-1,8-octanediamine in a yield of 96%, 95% or 95%, respectively. Another example started from a dialdehyde of 3(4),8(9)-tricyclo[5.2.1.0]decanedicarbaldehyde with use of a solvent of n-butanol, and obtained tricyclodecanedimethanamine in a yield of 96%.

The above process (1) which uses water as solvent has the problem of low yield of the desired diamine. The above processes (2) through (7) suggest that, in order to obtain a diamine at a high yield, it is suitable to use as solvent an alcohol, e.g. methanol, ethanol, 2-propanol, 1-butanol, isoamyl alcohol and n-octyl alcohol; an aromatic hydrocarbon, e.g. toluene; or an ether, e.g. methyl t-butyl ether, tetrahydrofuran and 1,4-dioxane.

The present inventors studied on the relationship between the solvent used and the reaction result and found that use of a solvent of an alkanol having at least 3 carbon atoms, an aromatic hydrocarbon such as toluene or an ether such as methyl t-butyl ether, tetrahydrofuran or 1,4-dioxane, as shown in Reference Example 1 of the present specification, leads to lower productivity and lower yields of the desired products, in comparison with reaction using a solvent of methanol or ethanol. This shows that it is most suitable, in order to produce diamines in high yield and productivity and commercially advantageously, to use methanol or ethanol as a solvent.

The present inventors then further studied how to produce diamines with use of a solvent of methanol or ethanol and, as a result, found that, under reaction conditions for synthesizing diamines, the solvent of methanol or ethanol gives rise to byproduction of a small amount of the corresponding methylamine or ethylamine, which is a primary amine having methyl or ethyl group. It was further found that these primary amines byproduced in small amounts will gradually accumulate in the alcohol recovered in a recovery process such as distillation separation, which is generally employed, upon using such an alcoholic solvent, not to dispose it after one use in view of economy and reduction of environmental load. These accumulated primary amines react with the starting material dialdehyde to form diamines with the hydrogen atoms of the amino groups replaced by methyl group or ethyl group. The resultant N-methyl or N-ethyl substituted diamines have properties such as boiling point similar to those of the desired diamine and hence can hardly be separated by distillation or like separation processes, thereby becoming impurities contained in the desired diamines. As a result, the obtained diamines will, when used as starting materials for polymers or chemicals, deteriorate the properties of the end products.

The above processes (2) through (5) and (7) never mention about the byproduction of primary amines from the alcoholic solvents used, accumulation of the primary amines in the alcoholic solvent in the course of recovery and re-use of the solvent or the accompanying formation of N-alkyl-substituted diamines, and take no countermeasures against such troubles. The above process (6), which mentions formation of N-alkyl-substituted diamines originating from the alcoholic solvents used though, never describes about selection of an optimum solvent of methanol or ethanol in view of yield and productivity as shown in Reference Example 1 of the present specification, or about any means for suppressing the formation of N-alkyl-substituted diamines originating from these alcoholic solvents.

SUMMARY OF THE INVENTION

An object of the present invention is to provide a process for producing diamines from dialdehydes in high yields and commercially advantageously, while using an alcohol as solvent and re-using it by recovery and minimizing formation of diamine impurities originating from the alcohol.

As a result of an intensive study how to suppress formation of N-alkyl-substituted diamines, which occurs during reductive amination of dialdehydes in a solvent of methanol or ethanol, from the primary amines originating from the alcohol, the present inventors have found, surprisingly, that the formation of the N-alkyl-substituted diamines can be suppressed by maintaining the molar ratio between ammonia and the primary amine at not less than a constant level, and completed the invention.

Thus, the present invention provides a process for producing diamines which comprises the steps of:

(1) reacting a dialdehyde with ammonia and hydrogen in the presence of an alcohol represented by the following general formula (I)

R—OH    (I)

wherein R represents methyl group or ethyl group (hereinafter referred to as "alcohol (I)") and a hydrogenation catalyst, to synthesize the corresponding diamine;
(2) separating and recovering the alcohol (I) by distilling the reaction mixture obtained in the step (1);
(3) separating the diamine by purifying the distillation residue obtained in the step (2); and
(4) feeding at least part of the alcohol (I) recovered in the step (2) to step (1);

said step (1) comprising maintaining the amount of ammonia at a level of at least 200 moles per mole of the primary amine represented by the following general formula (II)

R—NH$_2$    (II)

wherein R is as defined above (hereinafter referred to as "primary amine (II)") that has formed in the step (1) and accumulated in the reaction vessel for step (1).

DETAILED DESCRIPTION OF THE INVENTION

Examples of starting material dialdehydes are linear aliphatic dialdehydes, e.g. butanedial, hexanedial, octanedial, nonanedial, decanedial, undecanedial, dodecanedial, tetradecanedial, hexadecanedial, octadecanedial and eicosanedial; branched aliphatic dialdehydes, e.g. 2-methyloctanedial, 2-methylnonanedial and 2,7-dimethyloctanedial; alicyclic dials, e.g. 1,3-cyclohexanedicarbaldehyde, 1,4-cyclohexanedicarbaldehyde, 3(4),8(9)-tricyclo[5.2.1.0]-decanedicarbaldehyde and 2(3),5(6)-bicyclo[2.2.1] heptanedicarbaldehyde; and aromatic dialdehydes, e.g. terephthalaldehyde and isophthalaldehyde. These aldehydes are known and can readily be synthesized by, for example hydroformylation of unsaturated aldehydes having carbon atoms in a number smaller by one than that of the desired dialdehydes or diolefins having carbon atoms in a number smaller by 2 than that of the desired dialdehydes. The dialdehydes may also be obtained by reduction of ozone decomposition followed by reduction of cyclic olefins having the same number of carbon atoms, or by reduction of dicarboxylic acids having the same number of carbon atoms.

The concentration of the dialdehyde used is not particularly limited, but it is desirably in a range of 5 to 30% by weight based on the total weight of the liquid phase in the reaction vessel. If the concentration is less than 5% by weight, which lowers the volume efficiency of reaction and thus leads to low productivity, the amounts of ammonia and solvent recovered in the separation and purification processes of the obtained diamine will tend to increase, thus increasing load to equipment. As a result, the commercial merit will tend to be reduced. On the other hand, if the concentration exceeds 30% by weight, the amounts of byproducts in the reaction mixture, such as polymers, will tend to increase, thereby decreasing both the yield of the diamine and the activity of the hydrogenation catalyst used.

The alcohol (I) used as solvent is, concretely, methanol or ethanol. These solvents may be used in any amount with no specific restrictions but desirably in an amount ranging from 0.5 to 50 times the weight of the dialdehyde used, more preferably in an amount of 2 to 10 times the weight of the dialdehyde.

Examples of usable hydrogenation catalysts are Raney catalysts, e.g. Raney nickel, Raney cobalt and Raney copper; and supported catalysts comprising a metal having hydrogenation activity such as nickel, cobalt, platinum, palladium, rhodium, ruthenium or copper on a support such as Kieselguhr, silica, alumina, silica-alumina, clay, titania, zirconia, magnesia, calcia, lanthanum oxide, niobium oxide or carbon. These hydrogenation catalysts may have any shape such as powder, grains or pellets. The amount of the hydrogenation catalyst used may vary according to the desired reaction rate, but it is desirably in a range of 0.01 to 30% by weight based on the weight of the reaction mixture, more preferably in a range of 0.1 to 10% by weight on the same basis. The hydrogenation catalyst may be used in the form of suspension or as a fixed bed. The hydrogenation catalyst may be used after being subjected to activation treatment with hydrogen before the reaction.

It is necessary that ammonia be used in an amount of at least 200 moles per mole of the primary amine (II) that has formed from the alcohol present in the reaction vessel for step (1) This amount can sufficiently suppress formation of diamine impurities originating from the alcohol. The amount of ammonia used is preferably in a range of 2 to 300 moles, more preferably in a range of 5 to 100 moles, most preferably in a range of 5 to 50 moles, per mole of the dialdehyde used. If the amount of ammonia is less than 2 moles per mole of the dialdehyde, the yield of the desired diamine will tend to decrease; and if the amount exceeds 300 moles per mole of the dialdehyde, too large an apparatus will become necessary for recovering unreacted ammonia, thus leading to a disadvantage in practice.

The reaction temperature is desirably in a range of 40 to 200° C., more preferably in a range of 100 to 180° C. If the reaction temperature is lower than 40° C., the reaction will tend to proceed very slowly; and if the temperature is higher than 200° C., the amounts of polymers and like byproducts will tend to increase, thereby decreasing the yield.

The reaction pressure is, not specifically limited though, desirably in a range of 0.1 to 20 MPa in terms of hydrogen partial pressure, more preferably in a range of 0.5 to 15 MPa in the same terms. The hydrogen may either be added to make up for the consumption during the reaction or continuously circulated through the reaction zone.

The reaction can be carried out either batchwise or continuously. In either case, it is recommended to feed the dialdehyde used at a rate lower than the hydrogenation rate, i.e. at such a rate that assures no accumulation of the dialdehyde or reaction intermediates occurring in the reaction vessel. Thus, when a batch-type reactor is used, it is desirable to carry out reaction while feeding a dialdehyde or its solution in a solvent to a reaction vessel filled with a hydrogenation catalyst, a solvent, ammonia and hydrogen, at a rate lower than the hydrogenation rate. When a continuous operation is performed, it is desirable, for example, to effect reaction while feeding a dialdehyde or its solution in a solvent together with ammonia to a reaction vessel filled with a hydrogenation catalyst, a solvent and hydrogen, at a rate lower than the hydrogenation rate. In this case, the dialdehyde or its solution in a solvent may be fed to the reaction vessel either continuously at a constant rate or intermittently.

The above reaction gives a diamine corresponding to the dialdehyde used. Examples of the diamine are linear aliphatic diamines, e.g. butanediamine, hexanediamine, octanediamine, nonanediamine, decanediamine, undecanediamine, dodecanediamine, tetradecanediamine, hexadecanediamine, octadecanediamine and eicosanediamine; branched aliphatic diamines, e.g. 2-methyloctanediamine, 2-methylnonanediamine and 2,7-dimethyloctanediamine; alicyclic diamines, e.g. 1,3-cyclohexanedimethanamine, 1,4-cyclohexanedimethanamine, 3(4),8(9)-tricyclo[5.2.1.0] decanedimethanamine and 2(3),5(6)-bicyclo[2.2.1] heptanedimethanamine; and aromatic diamines, e.g. p-xylylenediamine and m-xylylenediamine.

Distillation of the reaction mixture obtained in step (1) separates and recovers ammonia at first and then separates and recovers the alcohol (I) used as solvent [step (2)]. The distillation residue gives, after being subjected to a purification process such as fine distillation or recrystallization, the diamine with high purity [step (3)]. At least part of the alcohol (I) obtained in step (2) is fed to step (1) again [step (4)], and used for the reaction in step (1). On this occasion, it is necessary, as described above, to adjust the amount of ammonia present in the reaction vessel for step (1) at a level of at least 200 moles per mole of the primary amine (II) that has formed from the alcohol (I) contained in the reaction vessel. This adjustment can suppress formation of N-alkyl-substituted diamine which would become impurity of the desired diamine. The adjustment of the molar ratio between ammonia and the primary diamine (II) present in the reaction vessel for step (1) may be carried out as follows. On distillation and recovery of the alcohol (I) in step (2), at least part of the primary amine (II) is removed from the alcohol (I) by further distillation and purification, and then the thus obtained purer alcohol (I) is fed to step (1) so that the ratio between ammonia and the primary amine (II) present in the reaction vessel for step (1) can be maintained within the above range. Or, alternatively, at first the content of the primary diamine (II) in the alcohol (I) recovered in step (2) is determined, and then the recovered alcohol is fed to step (1) while the amount of ammonia used in step (1) is adjusted such that the ratio between the ammonia and the primary amine (II) present in the reaction vessel for step (1) falls within the above range.

According to the present invention, diamines can be produced from dialdehydes in high yields and commercially advantageously, with use of a solvent of an alcohol, which is recovered and re-used, the obtained diamines having little diamine-based impurities originating from the re-used alcohol.

A further understanding of this invention can be obtained by reference to specific examples which are provided hereinbelow for purposes of illustration only and are not intended to be limitative of this invention.

In the Examples and Comparative Examples that follow, the quantitative analyses of the product diamines, ammonia, or byproduced primary amines (II) or N-alkyl-substituted diamines were carried out by the following methods.

(1) Determination of Diamines or N-Alkyl-Substituted Diamines

Diamines and N-alkyl-substituted diamines contained in a crude reaction mixture or distillation bottoms after solvent recovery were determined by gas chromatography analysis under the following conditions.

[Analysis Conditions]

Column: G-205 made by Chemicals Evaluation and Research Institute, Japan; length: 20 m; film thickness: 2.0 $\mu$m; diameter: 1.2 mm Temperature of injection and detection: 280° C.

Temperature elevation conditions programmed: 140° C. (maintained for 8 minutes)→10° C./minute→280° C. (maintained for 15 minutes)

(2) Determination of Ammonia

Quantitative analysis of ammonia that remained in the reaction vessel after completion of reaction was carried out according to the method using aqueous sulfuric acid, as follows. The gas present in the autoclave was passed through a 20% by weight aqueous sulfuric acid solution to trap the remaining ammonia. Nitrogen was then passed through the crude reaction mixture in the autoclave to purge the ammonia remaining in the crude reaction mixture, which ammonia was trapped in the aqueous sulfuric acid solution. The content of sulfuric acid in the solution after the trapping was determined by alkali titration. The obtained content value was then subtracted from the initial sulfuric acid content, to give the amount of sulfuric acid consumed for the ammonia trapping, from which the amount of ammonia trapped was calculated and taken as the amount of the remaining ammonia.

(3) Quantitative Determination of Primary Amines

Quantitative analysis of primary amines that remained in the reaction vessel after completion of reaction was carried out as follows. The aqueous sulfuric acid solution used for the determination of ammonia was treated with an excess of sodium hydroxide and then subjected to distillation for solvent recovery. The obtained distillates was combined with another distillates from distillation for solvent recovery of reaction mixture. The obtained mixture was subjected to gas chromatography under the following conditions.

[Analysis Conditions]

Column: capillary column CAM made by J & W Scientific Incorporated; length: 30 m; film thickness: 0.25 μm; diameter: 0.25 mm
Temperature of injection and detection: 40° C.
Temperature elevation conditions programmed: 35° C. (constant)

EXAMPLE 1

(The First Run of Repeated Reaction Runs)

A 300-ml autoclave equipped with an electromagnetic stirrer was charged with 63 g of methanol and 1.15 g of a nickel catalyst supported on Kieselguhr (nickel content: 52%). Hydrogen was introduced into the autoclave to a hydrogen partial pressure of 6 MPa and then the inside was heated to a temperature of 140° C. The catalyst was subjected to reduction treatment at this temperature for 2 hours. After the autoclave had been allowed to cool to room temperature, the hydrogen pressure was released. The autoclave was then charged with 30.6 g of ammonia and, while a hydrogen partial pressure of 3 MPa was applied, heated to a temperature of 140° C. Hydrogen was further introduced to a total pressure of 8.5 MPa. Thereafter, while hydrogen was being flown at a rate of 20 l/hour, 75 g of a methanolic solution obtained by dissolving 13.5 g of 1,9-nonanedial and 5.2 g of 2-methyl-1,8-octanedial in 56.3 g of methanol was fed through a high-pressure metering pump to the autoclave over 1 hour and 30 minutes. After completion of the feeding, hydrogen was further introduced with stirring for 1 hour at 140° C.

After completion of the reaction, the ammonia remaining in the autoclave was trapped with the aqueous sulfuric acid solution and its amount was determined to be 26.3 g. The crude reaction mixture was taken out and separated from the catalyst by filtration. Analysis of the obtained crude reaction mixture detected no trace of N-methyl-substituted compounds that would have been derived by introduction of methyl group into one of the nitrogen atoms of 1,9-nonanediamine or 2-methyl-1,8-octanediamine. Methanol distillates were recovered from the crude reaction mixture with a distillation apparatus equipped with a rectification column. The aqueous sulfuric acid solution having trapped ammonia was placed in a distillation apparatus equipped with a rectification column, from which ammonia and a small amount of methylamine were separated from sulfuric acid by addition of an excess of sodium hydroxide. The methanol containing the methylamine was then recovered by distillation. The recovered distillates weighed 116.0 g. Analysis of this methanol revealed that it contained 0.09 g of methylamine. By analysis of the bottoms after the distillation, it was found that 12.7 g of 1,9-nonanediamine (yield: 93%) and 4.9 g of 2-methyl-1,8-octanediamine (yield: 93%) had been obtained.

In this first run of repeated reaction runs, the autoclave contained 30.6 g of ammonia and no methylamine at the time of starting reaction. After the reaction, the autoclave contained 0.09 g of methylamine and 26.3 g of ammonia (533 moles per mole of methylamine).

(The Second Run of the Repeated Reaction Runs)

The second run was carried out in the same manner as in the first run except that the methanol recovered in the first run was used, as follows. To the recovered methanol distillates, new methanol was added in an amount just to supplement the loss having generated during distillation and other treatments, to a total amount of 119.3 g. The methanol was then divided into 63 g and 56.3 g, which were used for the initial feeding to the autoclave and for dissolving the starting material to be fed to the autoclave, respectively. After completion of the reaction, the ammonia remaining in the autoclave was trapped with the aqueous sulfuric acid solution and its amount was determined to be 26.2 g. The crude reaction mixture was taken out and separated from the catalyst by filtration. Analysis of the obtained crude reaction mixture detected no trace of N-methyl-substituted compounds that might have been formed by introduction of methyl group into one of the nitrogen atoms of 1,9-nonanediamine or 2-methyl-1,8-octanediamine. The solvent was recovered, in the same manner as in the first run, from the crude reaction mixture and the aqueous sulfuric acid solution having trapped ammonia, each with a distillation apparatus equipped with a rectification column. As a result 5.0 g of methanol distillates containing 0.08 g of methylamine and 112.3 g of methanol distillates containing 0.11 g of methylamine were recovered. Analysis of the bottoms after the distillation showed that the yields of 1,9-nonanediamine and 2-methyl-1,8-octanediamine were 92% and 92%, respectively.

In this second run of repeated reaction runs, the autoclave contained 0.09 g of methylamine and 30.6 g of ammonia (620 moles per mole of methylamine) at the time of starting reaction. After the reaction, the autoclave contained 0.19 g of methylamine and 26.2 g of ammonia (251 moles per mole of methylamine).

(The Third Run of the Repeated Reaction Runs)

The third run was carried out in the same manner as in the first run except that 112.3 g of the methanol containing 0.11 g of methylamine and recovered in the second run was used, as follows. To the recovered methanol distillates, new methanol was added in an amount just to supplement the loss, to a total amount of 119.3 g. The methanol was then divided into 63 g and 56.3 g, which were used for the initial feeding to the autoclave and for dissolving the starting material to be fed to the autoclave, respectively. After completion of the reaction, the ammonia remaining in the autoclave was trapped with the aqueous sulfuric acid solution and its amount was determined to be 26.5 g. The solvent was recovered in the same manner as in the first run. Analysis of the methanol recovered revealed that it contained 0.24 g of methylamine. The yields of the obtained 1,9-nonanediamine and 2-methyl-1,8-octanediamine were 92% and 91%, respectively. No trace of N-methyl-substituted compounds that might have been formed by introduction of methyl group into one of the nitrogen atoms of 1,9-nonanediamine or 2-methyl-1,8-octanediamine was detected.

In this third run of repeated reaction runs, the autoclave contained 0.11 g of methylamine and 30.6 g of ammonia (507 moles per mole of methylamine) at the time of starting reaction. After the reaction, the autoclave contained 0.24 g of methylamine and 26.5 g of ammonia (201 moles per mole of methylamine).

COMPARATIVE EXAMPLE 1

The first and second runs including solvent recovery were carried out in the same manner as in the first and second runs in Example 1. The third run was also carried out in the same manner as in the first run except that the methanol distillates recovered in the second run and containing a large amount of methylamine and those containing a small amount of methylamine were combined and used, as follows. To 117.0 g of the combined methanol distillates containing 0.19 g of methylamine, new methanol was added in an amount just to supplement the loss, to a total amount of 119.3 g. The methanol was then divided into 63 g and 56.3 g, which were used for the initial feeding to the autoclave and for dissolving the starting material to be fed to the autoclave, respectively. After completion of the reaction, the ammonia remaining in the autoclave was trapped with the aqueous sulfuric acid solution and its amount was determined to be 26.4 g. Solvent recovery was performed and the methanol recovered was analyzed to show that it contained 0.32 g of methylamine. The yields of the obtained 1,9-nonanediamine and 2-methyl-1,8-octanediamine were 92% and 92%, respectively. On this occasion, N-methyl-substituted compounds that had been formed by introduction of methyl group into one of the nitrogen atoms of 1,9-nonanediamine or 2-methyl-1,8-octanediamine was detected in an amount of 0.02 mole % based on the total moles of the product diamines.

In this third run of repeated reaction runs, the autoclave contained 0.19 g of methylamine and 30.6 g of ammonia (294 moles per mole of methylamine) at the time of starting reaction. After the reaction, the autoclave contained 0.32 g of methylamine and 26.4 g of ammonia (150 moles per mole of methylamine).

EXAMPLE 2

Repeated runs of reaction were carried out in the same manner as in Example 1 except that ethanol was used as solvent. In the solvent recovery step of the second run, 4.5 g of ethanol distillates containing 0.12 g of ethylamine and 113.0 g of those containing 0.17 g of ethylamine were recovered. This 113.0 g of ethanol containing 0.17 g of ethylamine and recovered in the second run was used for the third run. After completion of the third run, the ammonia remaining in the autoclave was trapped with the aqueous sulfuric acid solution and its amount was determined to be 26.8 g. Solvent recovery was performed and the ethanol recovered was analyzed to show that it contained 0.35 g of ethylamine. The yields of the obtained 1,9-nonanediamine and 2-methyl-1,8-octanediamine were 91% and 90%, respectively. On this occasion, no trace of N-ethyl-substituted compounds that might have been formed by introduction of ethyl group into one of the nitrogen atoms of 1,9-nonanediamine or 2-methyl-1,8-octanediamine was detected.

In this third run of repeated reaction runs, the autoclave contained 0.17 g of ethylamine and 30.6 g of ammonia (476 moles per mole of ethylamine) at the time of starting reaction. After the reaction, the autoclave contained 0.35 g of ethylamine and 26.8 g of ammonia (203 moles per mole of ethylamine).

COMPARATIVE EXAMPLE 2

The first and second runs were carried out in the same manner as in the first and second runs in Example 2. The third run was also carried out in the same manner as in the first run except that the ethanol distillates recovered in the second run and containing a large amount of ethylamine and those containing a small amount of ethylamine were combined and used, as follows. To 117.0 g of the combined ethanol distillates containing 0.29 g of ethylamine, new ethanol was added in an amount just to supplement the loss, to a total amount of 119.3 g. After completion of the reaction, the ammonia remaining in the autoclave was trapped with the aqueous sulfuric acid solution and its amount was determined to be 26.9 g. Solvent recovery was performed and the ethanol recovered was analyzed to show that it contained 0.46 g of ethylamine. The yields of the obtained 1,9-nonanediamine and 2-methyl-1,8-octanediamine were 91% and 91%, respectively. On this occasion, N-ethyl-substituted compounds that had been formed by introduction of ethyl group into one of the nitrogen atoms of 1,9-nonanediamine or 2-methyl-1,8-octanediamine were detected in an amount of 0.03 mole % based on the total moles of the product diamines.

In this third run of repeated reaction runs, the autoclave contained 0.29 g of ethylamine and 30.6 g of ammonia (279 moles per mole of ethylamine) at the time of starting reaction. After the reaction, the autoclave contained 0.46 g of ethylamine and 26.9 g of ammonia (155 moles per mole of ethylamine).

EXAMPLE 3

The first and second runs including solvent recovery were carried out in the same manner as in the first and second runs in Example 1. For the third run the methanol distillates recovered in the second run and containing a large amount of methylamine and those containing a small amount of methylamine were combined and used, as follows. To 116.5 g of the combined methanol distillates containing 0.18 g of methylamine, new methanol was added in an amount just to supplement the loss, to a total amount of 119.3 g. The methanol was then divided into 63 g and 56.3 g, which were used for the initial feeding to the autoclave and for dissolving the starting material to be fed to the autoclave, respectively. The third run was then carried out in the same manner as in the first run except that ammonia was fed in an amount of 38.5 g. After completion of the reaction, the ammonia remaining in the autoclave was trapped with the aqueous sulfuric acid solution and its amount was determined to be 34.8 g Solvent recovery was performed and the methanol recovered was analyzed to show that it contained 0.31 g of methylamine. The yields of the obtained 1,9-nonanediamine and 2-methyl-1,8-octanediamine were 92% and 92%, respectively. On this occasion, no trace of N-methyl-substituted compounds that might have been formed by introduction of methyl group into one of the nitrogen atoms of 1,9-nonanediamine or 2-methyl-1,8-octanediamine was detected.

In this third run of repeated reaction runs, the autoclave contained 0.18 g of methylamine and 38.5 g of ammonia (390 moles per mole of methylamine) at the time of starting reaction. After the reaction, the autoclave contained 0.31 g of methylamine and 34.8 g of ammonia (205 moles per mole of methylamine).

COMPARATIVE EXAMPLE 3

The first and second runs including solvent recovery were carried out in the same manner as in the first and second runs in Example 1. For the third run the methanol distillates recovered in the second run and containing a large amount of methylamine and those containing a small amount of methylamine were combined and used, as follows. To 116.5 g of the combined methanol distillates containing 0.18 g of methylamine, new methanol was added in an amount just to supplement the loss, to a total amount of 119.3 g. The methanol was then divided into 63 g and 56.3 g, which were used for the initial feeding to the autoclave and for dissolving the starting material to be fed to the autoclave, respectively. The third run was then carried out in the same manner as in the first run except that ammonia was fed in an amount of 19.3 g. After completion of the reaction, the ammonia remaining in the autoclave was trapped with the aqueous sulfuric acid solution and its amount was determined to be 15.3 g. Solvent recovery was performed and the methanol recovered was analyzed to show that it contained 0.30 g of methylamine. The yields of the obtained 1,9-nonanediamine and 2-methyl-1,8-octanediamine were 90% and 90%, respectively. On this occasion, N-methyl-substituted compounds that had been formed by introduction of methyl group into one of the nitrogen atoms of 1,9-nonanediamine or 2-methyl-1,8-octanediamine were detected in an amount of 0.10 mole % based on the total moles of the product diamines.

In this third run of repeated reaction runs, the autoclave contained 0.18 g of methylamine and 19.3 g of ammonia (196 moles per mole of methylamine) at the time of starting reaction. After the reaction, the autoclave contained 0.30 g of methylamine and 15.3 g of ammonia (93 moles per mole of methylamine).

EXAMPLE 4

Repeated runs of reaction were carried out in the same manner as in Example 1 except that 2.3 g of Raney nickel was used as catalyst. In the solvent recovery step of the second run, 5.0 g of methanol distillates containing 0.10 g of methylamine and 112.0 g of methanol distillates containing 0.12 g of methylamine were recovered. This 112.0 g of methanol containing 0.12 g of methylamine and recovered in the second run was used for the third run. After completion of the third run, the ammonia remaining in the autoclave was trapped with the aqueous sulfuric acid solution and its amount was determined to be 26.6 g. Solvent recovery was performed and the methanol recovered was analyzed to show that it contained 0.24 g of methylamine. The yields of the obtained 1,9-nonanediamine and 2-methyl-1,8-octanediamine were 92% and 92%, respectively. On this occasion, no trace of N-methyl-substituted compounds that might have been formed by introduction of methyl group into one of the nitrogen atoms of 1,9-nonanediamine or 2-methyl-1,8-octanediamine was detected.

In this third run of repeated reaction runs, the autoclave contained 0.12 g of methylamine and 30.6 g of ammonia (465 moles per mole of methylamine) at the time of starting reaction. After the reaction, the autoclave contained 0.24 g of methylamine and 26.6 g of ammonia (202 moles per mole of methylamine).

COMPARATIVE EXAMPLE 4

The first and second runs including solvent recovery were carried out in the same manner as in the first and second runs in Example 4. The third run was carried out in the same manner as in the first run except that the methanol distillates recovered in the second run and containing a large amount of methylamine and those containing a small amount of methylamine were combined and used. That is, to 117.0 g of the combined methanol distillates containing 0.22 g of methylamine, new methanol was added in an amount just to supplement the loss, to a total amount of 119.3 g. After completion of the reaction, the ammonia remaining in the autoclave was trapped with the aqueous sulfuric acid solution and its amount was determined to be 26.5 g. Solvent recovery was performed and the methanol recovered was analyzed to show that it contained 0.34 g of methylamine. The yields of the obtained 1,9-nonanediamine and 2-methyl-1,8-octanediamine were 91% and 91%, respectively. On this occasion, N-methyl-substituted compounds that had been formed by introduction of methyl group into one of the nitrogen atoms of 1,9-nonanediamine or 2-methyl-1,8-octanediamine were detected in an amount of 0.05 mole % based on the total moles of the product diamines.

In this third run of repeated reaction runs, the autoclave contained 0.22 g of methylamine and 30.6 g of ammonia (254 moles per mole of methylamine) at the time of starting reaction. After the reaction, the autoclave contained 0.34 g of methylamine and 26.5 g of ammonia (142 moles per mole of methylamine).

EXAMPLE 5

Repeated runs of reaction were carried out in the same manner as in Example 1 except that 5.5 g of nickel catalyst supported on Kieselguhr was used and that the reaction temperature was set at 100° C. In the solvent recovery step of the second run, 5.0 g of methanol distillates containing 0.07 g of methylamine and 112.0 g of methanol distillates containing 0.10 g of methylamine were recovered. This 112.0 g of methanol containing 0.10 g of methylamine and recovered in the second run was used for the third run. After completion of the third run, the ammonia remaining in the autoclave was trapped with the aqueous sulfuric acid solution and its amount w-as determined to be 26.3 g. Solvent recovery was performed and the methanol recovered was analyzed to show that it contained 0.22 g of methylamine. The yields of the obtained 1,9-nonanediamine and 2-methyl-1,8-octanediamine were 90% and 90%, respectively. On this occasion, no trace of N-methyl-substituted compounds that might have been formed by introduction of methyl group into one of the nitrogen atoms of 1,9-nonanediamine or 2-methyl-1,8-octanediamine was detected.

In this third run of repeated reaction runs, the autoclave contained 0.10 g of methylamine and 30.6 g of ammonia (558 moles per mole of methylamine) at the time of starting reaction. After the reaction, the autoclave contained 0.22 g of methylamine and 26.3 g of ammonia (218 moles per mole of methylamine).

COMPARATIVE EXAMPLE 5

The first and second runs including solvent recovery were carried out in the same manner as in the first and second runs in Example 5. The third run was carried out in the same manner as in the first run except that the methanol distillates recovered in the second run and containing a large amount of methylamine and those containing a small amount of methylamine were combined and used. That is, to 117.0 g of the combined methanol distillates containing 0.17 g of methylamine, new methanol was added in an amount just to supplement the loss, to a total amount of 119.3 g. After completion of the reaction, the ammonia remaining in the autoclave was trapped with the aqueous sulfuric acid solution and its amount was determined to be 26.5 g. Solvent recovery was performed and the methanol recovered was analyzed to show that it contained 0.30 g of methylamine. The yields of the obtained 1,9-nonanediamine and 2-methyl-1,8-octanediamine were 92% and 92%, respectively. On this occasion, N-methyl-substituted compounds that had been formed by introduction of methyl group into one of the nitrogen atoms of 1,9-nonanediamine or 2-methyl-1,8-octanediamine were detected in an amount of 0.03 mole % based on the total moles of the product diamines.

In this third run of repeated reaction runs, the autoclave contained 0.17 g of methylamine and 30.6 g of ammonia (328 moles per mole of methylamine) at the time of starting reaction. After the reaction, the autoclave contained 0.30 g of methylamine and 26.5 g of ammonia (161 moles per mole of methylamine).

EXAMPLE 6

Repeated runs of reaction were carried out in the same manner as in Example 1 except that 0.35 g of nickel catalyst supported on Kieselguhr was used and that the reaction temperature was set at 180° C. In the solvent recovery step of the second run, 5.0 g of methanol distillates containing 0.10 g of methylamine and 112.0 g of methanol distillates containing 0.13 g of methylamine were recovered. This 112.0 g of methanol containing 0.13 g of methylamine and recovered in the second run was used for the third run. After completion of the third run, the ammonia remaining in the autoclave was trapped with the aqueous sulfuric acid solution and its amount was determined to be 26.8 g. Solvent recovery was performed and the methanol recovered was analyzed to show that it contained 0.24 g of methylamine. The yields of the obtained 1,9-nonanediamine and 2-methyl-1,8-octanediamine were 91% and 91%, respectively. On this occasion, no trace of N-methyl-substituted compounds that might have been formed by introduction of methyl group into one of the nitrogen atoms of 1,9-nonanediamine or 2-methyl-1,8-octanediamine was detected.

In this third run of repeated reaction runs, the autoclave contained 0.13 g of methylamine and 30.6 g of ammonia (429 moles per mole of methylamine) at the time of starting reaction. After the reaction, the autoclave contained 0.24 g of methylamine and 26.8 g of ammonia (204 moles per mole of methylamine).

COMPARATIVE EXAMPLE 6

The first and second runs were carried out in the same manner as in the first and second runs in Example 6. The third run was carried out in the same manner as in the first run except that the methanol distillates recovered in the second run and containing a large amount of methylamine and those containing a small amount of methylamine were combined and used. That is, to 117.0 g of the combined methanol distillates containing 0.23 g of methylamine, new methanol was added in an amount just to supplement the loss, to a total amount of 119.3 g. After completion of the reaction, the ammonia remaining in the autoclave was trapped with the aqueous sulfuric acid solution and its amount was determined to be 26.5 g. Solvent recovery was performed and the methanol recovered was analyzed to show that it contained 0.34 g of methylamine. The yields of the obtained 1,9-nonanediamine and 2-methyl-1,8-octanediamine were 91% and 91%, respectively. On this occasion, N-methyl-substituted compounds that had been formed by introduction of methyl group into one of the nitrogen atoms of 1,9-nonanediamine or 2-methyl-1,8-octanediamine were detected in an amount of 0.03 mole % based on the total moles of the product diamines.

In this third run of repeated reaction runs, the autoclave contained 0.23 g of methylamine and 30.6 g of ammonia (243 moles per mole of methylamine) at the time of starting reaction. After the reaction, the autoclave contained 0.34 g of methylamine and 26.5 g of ammonia (142 moles per mole of methylamine).

EXAMPLE 7

Repeated runs of reaction were carried out in the same manner as in Example 1 except that the total pressure in the autoclave was set at 5.5 MPa. In the solvent recovery step of the second run, 5.0 g of methanol distillates containing 0.08 g of methylamine and 112.0 g of methanol distillates containing 0.11 g of methylamine were recovered. This 112.0 g of methanol containing 0.11 g of methylamine and recovered in the second run was used for the third run. After completion of the third run, the ammonia remaining in the autoclave was trapped with the aqueous sulfuric acid solution and its amount was determined to be 26.7 g. Solvent recovery was performed and the methanol recovered was analyzed to show that it contained 0.24 g of methylamine. The yields of the obtained 1,9-nonanediamine and 2-methyl-1,8-octanediamine were 90% and 90%, respectively. On this occasion, no trace of N-methyl-substituted compounds that might have been formed by introduction of methyl group into one of the nitrogen atoms of 1,9-nonanediamine or 2-methyl-1,8-octanediamine was detected.

In this third run of repeated reaction runs, the autoclave contained 0.11 g of methylamine and 30.6 g of ammonia (507 moles per mole of methylamine) at the time of starting reaction. After the reaction, the autoclave contained 0.24 g of methylamine and 26.7 g of ammonia (203 moles per mole of methylamine).

COMPARATIVE EXAMPLE 7

The first and second runs were carried out in the same manner as in the first and second runs in Example 7. The third run was carried out in the same manner as in the first run except that the methanol distillates recovered in the second run and containing a large amount of methylamine and those containing a small amount of methylamine were combined and used. That is, to 117.0 g of the combined methanol distillates containing 0.19 g of methylamine, new methanol was added in an amount just to supplement the loss, to a total amount of 119.3 g. After completion of the reaction, the ammonia remaining in the autoclave was trapped with the aqueous sulfuric acid solution and its amount was determined to be 26.3 g. Solvent recovery was performed and the methanol recovered was analyzed to show that it contained 0.32 g of methylamine. The yields of the obtained 1,9-nonanediamine and 2-methyl-1,8-octanediamine were 91% and 91%, respectively. On this occasion, N-methyl-substituted compounds that had been formed by introduction of methyl group into one of the nitrogen atoms of 1,9-nonanediamine or 2-methyl-1,8-octanediamine were detected in an amount of 0.02 mole % based on the total moles of the product diamines.

In this third run of repeated reaction runs, the autoclave contained 0.19 g of methylamine and 30.6 g of ammonia (294 moles per mole of methylamine) at the time of starting reaction. After the reaction, the autoclave contained 0.32 g of methylamine and 26.3 g of ammonia (150 moles per mole of methylamine).

EXAMPLE 8

Repeated runs of reaction were carried out in the same manner as in Example 1 except that the total pressure in the autoclave was set at 18 MPa. In the solvent recovery step of the second run, 5.0 g of methanol distillates containing 0.10 g of methylamine and 112.0 g of methanol distillates containing 0.13 g of methylamine were recovered. This 112.0 g of methanol containing 0.13 g of methylamine and recovered in the second run was used for the third run. After completion of the third run, the ammonia remaining in the autoclave was trapped with the aqueous sulfuric acid solution and its amount was determined to be 26.9 g. Solvent recovery was performed and the methanol recovered was analyzed to show that it contained 0.24 g of methylamine. The yields of the obtained 1,9-nonanediamine and 2-methyl-1,8-octanediamine were 90% and 90%, respectively. On this occasion, no trace of N-methyl-substituted compounds that might have been formed by introduction of methyl group into one of the nitrogen atoms of 1,9-nonanediamine or 2-methyl-1,8-octanediamine was detected.

In this third run of repeated reaction runs, the autoclave contained 0.13 g of methylamine and 30.6 g of ammonia (429 moles per mole of methylamine) at the time of starting reaction. After the reaction, the autoclave contained 0.24 g of methylamine and 26.9 g of ammonia (204 moles per mole of methylamine).

COMPARATIVE EXAMPLE 8

The first and second runs were carried out in the same manner as in the first and second runs in Example 8. The third run was carried out in the same manner as in the first run except that the methanol distillates recovered in the second run and containing a large amount of methylamine and those containing a small amount of methylamine were combined and used. That is, to 117.0 g of the combined methanol distillates containing 0.23 g of methylamine, new methanol was added in an amount just to supplement the loss, to a total amount of 119.3 g. After completion of the reaction, the ammonia remaining in the autoclave was trapped with the aqueous sulfuric acid solution and its amount was determined to be 26.4 g. Solvent recovery was performed and the methanol recovered was analyzed to show that it contained 0.34 g of methylamine. The yields of the obtained 1,9-nonanediamine and 2-methyl-1,8-octanediamine were 92% and 92%, respectively. On this occasion, N-methyl-substituted compounds that had been formed by introduction of methyl group into one of the nitrogen atoms of 1,9-nonanediamine or 2-methyl-1,8-octanediamine were detected in an amount of 0.03 mole % based on the total moles of the product diamines.

In this third run of repeated reaction runs, the autoclave contained 0.23 g of methylamine and 30.6 g of ammonia (243 moles per mole of methylamine) at the time of starting reaction. After the reaction, the autoclave contained 0.34 g of methylamine and 26.4 g of ammonia (142 moles per mole of methylamine).

EXAMPLE 9

Repeated runs of reaction were carried out in the same manner as in Example 1 except that the starting material fed to the reaction vessel was changed to 13.7 g of 1,6-hexanedial. In the solvent recovery step of the second run, 5.0 g of methanol distillates containing 0.09 g of methylamine and 112.0 g of methanol distillates containing 0.13 g of methylamine were recovered. This 112.0 g of methanol containing 0.13 g of methylamine and recovered in the second run was used for the third run. After completion of the third run, the ammonia remaining in the autoclave was trapped with the aqueous sulfuric acid solution and its amount was determined to be 26.5 g. Solvent recovery was performed and the methanol recovered was analyzed to show that it contained 0.23 g of methylamine. The yield of the obtained 1,6-hexanediamine was 92%. On this occasion, no trace of N-methyl-substituted compound that might have been formed by introduction of methyl group into one of the nitrogen atoms of 1,6-hexanediamine was detected.

In this third run of repeated reaction runs, the autoclave contained 0.13 g of methylamine and 30.6 g of ammonia (429 moles per mole of methylamine) at the time of starting reaction. After the reaction, the autoclave contained 0.23 g of methylamine and 26.5 g of ammonia (210 moles per mole of methylamine).

EXAMPLE 10

Repeated runs of reaction were carried out in the same manner as in Example 1 except that the starting material fed to the reaction vessel was changed to 23.0 g of 3(4),8(9)-tricyclo[5.2.1.0]decanedicarbaldehyde. In the solvent recovery step of the second run, 5.0 g of methanol distillates containing 0.08 g of methylamine and 112.0 g of methanol distillates containing 0.11 g of methylamine were recovered. This 112.0 g of methanol containing 0.11 g of methylamine and recovered in the second run was used for the third run. After completion of the third run, the ammonia remaining in the autoclave was trapped with the aqueous sulfuric acid solution and its amount was determined to be 26.7 g. Solvent recovery was performed and the methanol recovered was analyzed to show that it contained 0.22 g of methylamine. The yield of the obtained 3(4),8(9)-tricyclo[5.2.1.0] decanedimethanamine was 90%. On this occasion, no trace of N-methyl-substituted compound that might have been formed by introduction of methyl group into one of the nitrogen atoms of 3(4),8(9)-tricyclo[5.2.1.0] decanedimethanamine was detected.

In this third run of repeated reaction runs, the autoclave contained 0.11 g of methylamine and 30.6 g of ammonia (507 moles per mole of methylamine) at the time of starting reaction. After the reaction, the autoclave contained 0.22 g of methylamine and 26.7 g of ammonia (221 moles per mole of methylamine).

REFERENCE EXAMPLE 1

An autoclave equipped with a sampling tube having a filter was used and the first run of Example 1 was repeated with solvents as shown in Table 1. Samples were taken from the reaction mixtures just after the feeding of starting materials and after further reaction at 140° C. for one hour after the feeding and checked for the yield of the desired products. The results are also shown in Table 1.

TABLE 1

| | Yield (%) | |
|---|---|---|
| Solvent | Just after feeding | 1 hour later |
| Methanol | 90 | 93 |
| Ethanol | 89 | 91 |
| 1-Propanol | 73 | 81 |
| 1-Butanol | 65 | 86 |
| Isoamyl alcohol | 56 | 85 |
| n-Octanol | 44 | 83 |
| Toluene | 34 | 84 |
| Methyl t-butyl ether | 51 | 83 |
| Tetrahydrofuran | 45 | 85 |
| 1,4-Dioxane | 47 | 86 |

Obviously, numerous modifications and variations of the present invention are possible in light of the above teachings. It is therefore to be understood that within the scope of the appended claims, the invention may be practiced otherwise than as specifically described herein.

What is claimed is:

1. A process for producing diamines which comprises the steps of:
   (1) reacting a dialdehyde with ammonia and hydrogen in the presence of an alcohol represented by the following general formula (I)

R—OH       (I)

wherein R represents methyl group or ethyl group, and a hydrogenation catalyst, to synthesize the corresponding diamine;
   (2) separating and recovering said alcohol by distilling the reaction mixture obtained in the step (1);

(3) separating the diamine by purifying the distillation residue obtained in the step (2); and (4) feeding at least part of said alcohol recovered in the step (2) to the step (1);

said step (1) comprising maintaining the amount of ammonia at a level of at least 200 moles per mole of the primary amine represented by the following general formula (II)

R—NH$_2$        (II)

wherein R is as defined above that has formed in the step (1) and accumulated in the reaction vessel for step (1).

2. The process according to claim 1, wherein said dialdehyde is a linear aliphatic aldehyde, a branched aliphatic dialdehyde, an alicyclic dialdehyde or an aromatic dialdehyde.

3. The process according to claim 2, wherein said linear aliphatic dialdehyde is butanedial, hexanedial, octanedial, nonanedial, decanedial, undecanedial, dodecanedial, tetradecanedial, hexadecanedial, octadecanedial or eicosanedial; said branched aliphatic dialdehyde is 2-methyloctanedial, 2-methylnonanedial or 2,7-dimethyloctanedial; said alicyclic dialdehyde is 1,3-cyclohexanedicarbaldehyde, 1,4-cyclohexanedicarbaldehyde, 3(4),8(9)-tricyclo[5.2.1.0]decanedicarbaldehyde or 2(3),5(6)-bicyclo[2.2.1]heptanedicarbaldehyde;, and said aromatic dialdehyde is terephthalaldehyde or isophthalaldehyde.

4. The process according to claim 1, wherein said dialdehyde is a mixture of a linear aliphatic dialdehyde and a branched aliphatic dialdehyde.

5. The process according to claim 4, wherein said linear aliphatic dialdehyde is 1,9-nonanedial and said branched aliphatic dialdehyde is 2-methyl-1,8-octanedial.

6. The process according to claim 1, wherein the concentration of said dialdehyde is in a range of 5 to 30% by weight based on the total weight of the liquid phase in the reaction vessel.

7. The process according to claim 1, wherein the amount of said alcohol used is in a range of 0.5 to 50 times by weight based on the weight of said dialdehyde.

8. The process according to claim 7, wherein the amount of said alcohol used is in a range of 2 to 10 times by weight based on the weight of said dialdehyde.

9. The process according to claim 1, wherein said hydrogenation catalyst is a Raney catalyst or a supported catalyst comprising a metal having hydrogenation activity on a support.

10. The process according to claim 9, wherein said Raney catalyst is Raney nickel, Raney cobalt or Raney copper, and said supported catalyst is nickel, cobalt, platinum, palladium, rhodium, ruthenium or copper supported on Kieselguhr, silica, alumina, silica-alumina, clay, titania, zirconia, magnesia, calcia, lanthanum oxide, niobium oxide or carbon.

11. The process according to claim 1, wherein the amount of said hydrogenation catalyst is in a range of 0.01 to 30% by weight based on the total weight of the liquid phase in the reaction vessel.

12. The process according to claim 11, wherein the amount of said hydrogenation catalyst is in a range of 0.1 to 10% by weight based on the total weight of the liquid phase in the reaction vessel.

13. The process according to claim 1, wherein the amount of ammonia is in a range of 2 to 300 moles per mole of said dialdehyde.

14. The process according to claim 13, wherein the amount of ammonia is in a range of 5 to 100 moles per mole of said dialdehyde.

15. The process according to claim 14, wherein the amount of ammonia is in a range of 5 to 50 moles per mole of said dialdehyde.

16. The process according to claim 1, wherein the reaction temperature is in a range of 40 to 200° C.

17. The process according to claim 16, wherein the reaction temperature is in a range of 100 to 180° C.

18. The process according to claim 1, wherein the reaction pressure is 0.1 to 20 MPa in terms of hydrogen partial pressure.

19. The process according to claim 18, wherein the reaction pressure is 0.5 to 15 MPa in terms of hydrogen partial pressure.

* * * * *